United States Patent [19]

Timmler et al.

[11] 4,102,891
[45] Jul. 25, 1978

[54] 1-(2-HALOGENO-2-PHENYL-ETHYL)-TRIAZOLES

[75] Inventors: Helmut Timmler; Karl Heinz Büchel, both of Wuppertal; Wilhelm Brandes, Cologne; Paul-Ernst Frohberger, Leverkusen, all of Germany

[73] Assignee: Bayer Aktiengesellschaft, Leverkusen, Germany

[21] Appl. No.: 729,930

[22] Filed: Oct. 6, 1976

[30] Foreign Application Priority Data

Oct. 27, 1975 [DE] Fed. Rep. of Germany ....... 2547954

[51] Int. Cl.$^2$ .................. A01N 9/22; A61K 31/41; C07D 249/08
[52] U.S. Cl. .................. 260/308 R; 424/269; 424/232
[58] Field of Search .................. 260/308 R; 424/269

[56] References Cited

U.S. PATENT DOCUMENTS

| 3,679,697 | 7/1972 | Kreider | 260/309 |
| 3,755,349 | 8/1973 | Timmler et al. | 424/269 |
| 3,897,438 | 7/1975 | Draber et al. | 260/308 R |

Primary Examiner—Alton D. Rollins
Attorney, Agent, or Firm—Burgess, Dinklage & Sprung

[57] ABSTRACT 1-(2-Halogeno-2-phenyl-ethyl)-triazoles of the formula

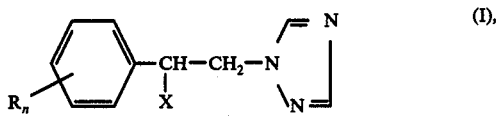

in which
X represents halogen,
R represents halogen, alkyl, alkoxy, alkylthio, alkylsulfonyl, halogenoalkyl, nitro, cyano, optionally substituted phenyl or optionally substituted phenoxy and
n is 0, 1, 2 or 3,
or salts thereof, which possess fungicidal properties.

4 Claims, No Drawings

1-(2-HALOGENO-2-PHENYL-ETHYL)-TRIAZOLES

The present invention relates to and has for its objects the provision of particular new substituted 1-(2-halogeno-2-phenyl-ethyl)-triazoles or salts thereof which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in U.S. Pat. No. 3,679,697 that 1(β-halogeno-phenylethyl)-imidazoles, such as, for example, 1-(β-chloro-phenylethyl)imidazole nitrate (Compound A), exhibit fungicidal activity. However, in certain applications their action is not always entirely satisfactory, especially if low amounts and low concentrations are used.

Furthermore, it is known from Phytopathology 33, 1113 (1963) that zinc ethylene-1,2-bis-dithiocarbamate (Compound B), is a good agent for combating fungal diseases of plants. However, its use as a seed dressing is only possible with limitations, since its activity is low when low amounts and low concentrations are used.

The present invention provides, as new compounds, the 1-(2-halogeno-2-phenylethyl)-triazoles of the general formula

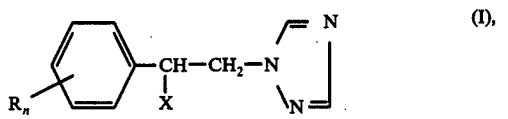

in which

X represents halogen,

R represents halogen, alkyl, alkoxy, alkylthio, alkylsulfonyl, halogenoalkyl, nitro, cyano, optionally substituted phenyl or optionally substituted phenoxy and n is 0, 1, 2 or 3, and their salts.

Preferably, R represents halogen (especially fluorine, chlorine or bromine), nitro, cyano, alkyl or alkyl-sulfonyl each with 1 to 4 carbon atoms, alkoxy or alkylthio each with 1 or 2 carbon atoms, halogenoalkyl with up to 4 carbon atoms and up to 5 halogen atoms (especially with up to 2 carbon atoms and up to 3 identical or different halogen atoms, preferred halogens being fluorine and chlorine as in, for example, trifluoromethyl), or phenyl or phenoxy which two last-mentioned radicals can optionally carry one or more substituents selected from halogen (especially fluorine, chlorine or bromine), cyano, nitro and halogenoalkyl with up to 2 carbon atoms and up to 3 identical or different halogen atoms (the preferred halogens being fluorine and chlorine as in, for example, trifluoromethyl).

Surprisingly, the 1-(2-halogeno-2-phenyl-ethyl)-triazoles according to the invention exhibit a substantially greater fungicidal activity, especially against species of rust and mildew, than the 1-(β-halogeno-phenylethyl)imidazoles known from the state of the art, for example 1-(β-chloro-phenylethyl)-imidazole, which, chemically and in respect of their action, are the nearest compounds, and than zinc ethylene-1,2-bis-dithiocarbamate, which is a known compound of the same type of action. The active compounds according to the invention thus represent an enrichment of the art.

The present invention also provides a process for the preparation of a 1-(2-halogeno-2-phenyl-ethyl)-triazoles of the formula (I), in which a 1-(2-hydroxy-2-phenyl-ethyl)traizole of the general formula

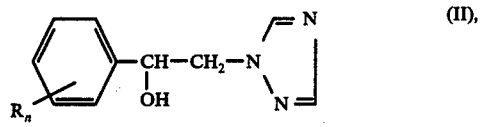

in which

R and n have the abovementioned meanings, is reacted with an agent which splits off halogen, if appropriate in the presence of a diluent. The triazole (I) thus formed is in the form of a hydrohalide salt; this may be converted into the triazole itself and thence into any other salt in known manner.

If 1-[2-(4'-chlorophenyl)-2-hydroxy-ethyl]-1,2,4-triazole and thionyl chloride are used as starting materials, the course of the reaction can be represented by the following equation:

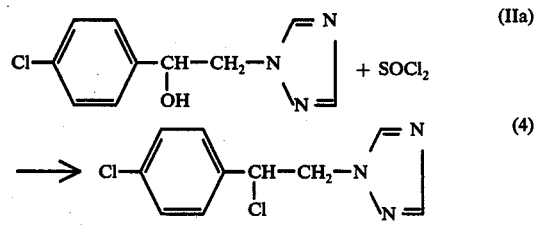

The starting materials of the formula (II) have not previously been described in the literature. However, in part they are the subject of U.S. patent application Ser. No. 586,121, filed June 11, 1975, now abandoned. They are obtained by reduction of the corresponding triazoly-lalkanones of the formula

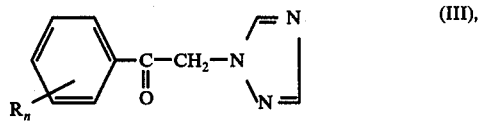

in which

R and n have the abovementioned meanings, by means of aluminum isopropylate, with formamidine-sulfinic acid and alkali metal hydroxides, or with complex hydrides, as illustrated, for example, in examples hereinbelow.

The compounds of the formula (III) are also new. Their preparation is also a subject of the abovementioned pending application. They are obtained, for example, by reacting halogenoketones of the formula

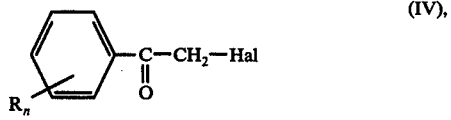

in which

R and n have the abovementioned meanings and

Hal represents chlorine or bromine, with 1,2,4-triazole in the presence of an acid-binding agent, as also illustrated in the preparative examples hereinbelow.

The halogenoketones of the formula (IV) are known from Bulletin de la Societe Chimique de France 1955, pages 1363-1383 and can be prepared in accordance with the processes described there; in this context, see also the data in U.S. Pat. No. 3,679,697 and in German Offenlegungsschrift (German Published Specification) No. 2,063,857.

The following may be mentioned, for instance, as examples of the 1-(2-hydroxy-2-phenyl-ethyl)-triazoles of the formula (II) to be used as starting materials according to the invention: 1-(2-hydroxy-2-phenyl-ethyl)-1,2,4-triazole, 1-(2-hydroxy-2-(2'-methylphenyl)-ethyl)-1,2,4-triazole, 1-(2-hydroxy-2-(2'-ethyl-4'-chlorophenyl)-ethyl)-1,2,4-triazole, 1-(2-hydroxy-2-(4'-trifluoromethylphenyl)-ethyl)-1,2,4-triazole, 1-(2-hydroxy-2-(4'-nitrophenyl)-ethyl)-1,2,4-triazole, 1-(2-hydroxy-2-(2'-fluorophenyl)-ethyl)-1,2,4-triazole, 1-(2-hydroxy-2-(2'-chlorophenyl)-ethyl)-1,2,4-triazole, 1-(2-hydroxy-2-(2',4'-dichlorophenyl)-ethyl)-1,2,4-triazole, 1-(2-hydroxy-2-(4'-bromophenyl)-ethyl)-1,2,4-triazole, 1-(2-hydroxy-2-(3'-iodophenyl)-ethyl)-1,2,4-triazole, 1-(2-hydroxy-2-(4'-cyanophenyl)-ethyl)-1,2,4-triazole, 1-(2-hydroxy-2-(2'-methoxyphenyl)-ethyl)-1,2,4-triazole, 1-(2-hydroxy-2-(2'-ethylthiophenyl)-ethyl)-1,2,4-triazole, 1-(2-hydroxy-2-(4'-methylsulfonylphenyl)-ethyl)-1,2,4-triazole, 1-(2-hydroxy- 2-(2',4',5'-trichlorophenyl)-ethyl)-1,2,4-triazole, 1-(2-hydroxy-2-(4'-biphenylyl)-ethyl)-1,2,4-triazole, 1-(2-hydroxy-2-(4''-chloro-4'-biphenylyl)-ethyl)-1,2,4-triazole, 1-(2-hydroxy-2-(2'',4''-dichloro-4'-biphenylyl)-ethyl)-1,2,4-traizole, 1-(2-hydroxy-2-(2''-fluoro-2'-biphenylyl)-ethyl)-1,2,4-triazole, 1-(2-hydroxy-2-(4''-trifluoromethyl-4'-biphenylyl)-ethyl)-1,2,4-triazole, 1-(2-hydroxy-2-(4'-phenoxyphenyl)-ethyl)-1,2,4-triazole, 1-(2-hydroxy-2-[4'-(4''-chlorophenoxy)-phenyl]-ethyl)-1,2,4-triazole, 1-(2-hydroxy-2-[4'-(2'',4''-dichlorophenoxy)-phenyl]-ethyl)-1,2,4-triazole, 1-(2-hydroxy-2-[4'-(3''-nitrophenoxy)-phenyl]-ethyl)-1,2,4-triazole and 1-(2-hydroxy-2-[4'-(4''-bromophenoxy)-phenyl]-ethyl)-1,2,4-triazole.

The halogenating agents, which are also required for the preparation of the triazoles according to the invention, determine the substituent X in the formula (I). Preferred halogenating agents which may be mentioned are phosphorus trichloride, phosphorus tribromide, phosphorus pentachloride, anhydrous hydrofluoric acid and, especially, thionyl chloride.

Preferred salts of the compounds of the formula (I) are salts with physiologically tolerated acids, especially the hydrogen halide acids, such as, for example, hydrochloric acid and hydrobromic acid, as well as phosphoric acid and nitric acid, and also monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and finally sulfonic acids, such as 1,5-naphthalenedisulfonic acid.

Diluents which can be used for the reaction according to the invention are all inert organic solvents, especially ketones, such as diethyl ketone and, especially, acetone and methyl ethyl ketone; ethers, such as diethyl ether and dioxane; benzene; and chlorinated hydrocarbons, such as chloroform, methylene chloride or carbon tetrachloride.

The reaction temperatures can be varied within a fairly wide range. In general, the reaction is carried out at between 20° and 100° C, preferably at the boiling point of the solvent.

In carrying out the process according to the invention, preferably 1to 2 moles of agent which splits off halogen are employed per mole of the triazole of the formula (II). The compounds of the formula (I) are obtained in the form of their hydrohalides and can be isolated as such, by precipitating them by addition of an organic solvent, for example toluene, filtering them off and, if appropriate, purifying them by recrystallization. The compounds of the formula (I) can also be isolated in the form of their free base. For this purpose the corresponding hydrohalides are dissolved in water and the free base is precipitated by adding sodium bicarbonate, taken up by means of an organic solvent and isolated in accordance with customary methods. The free base of the formula (I) can also be obtained without isolating the hydrohalides, by removing the excess halogenating agent, for example by distillation, adding aqueous sodium bicarbonate solution directly to the reaction mixture and extracting the base by shaking with a solvent. The other salts of the compounds of the formula (I) can be obtained from the bases in a simple manner in accordance with customary methods of forming salts, for example by dissolving the base in ether, for example diethyl ether, and adding the acid, for example nitric acid, and can be isolated in a known manner, for example by filtering off, and be purified if appropriate, all as illustrated in the preparative examples hereinbelow.

The active compounds according to the invention exhibit a powerful fungitoxic action. They do not harm crop plants in the concentrations required for combating fungi. For this reason they are suitable for use as plant protection agents for combating fungi. Fungitoxic agents are employed in plant protection for combating Archimycetes, Phycomycetes, Ascomycetes, Basidiomycetes and Fungi Imperfecti.

The active compounds according to the invention have a broad spectrum of action and can be employed against parasitic fungi which attack the above-ground parts of the plants or attack the plants through the soil, and also against seedborne pathogens.

They display a particularly good activity against parasitic fungi on above-ground parts of plants, such as species of Erysiphe, species of Podosphaera and species of Venturia, for example against the pathogen of powdery mildew of apples (*Podosphaera leucotricha*) and of the apple scab (*Fusicladium dendriticum*). They furthermore exhibit a high activity against cereal diseases, such as against powdery mildew of cereals and against cereal rust.

In addition, it should be pointed out that some of the compounds exhibit a systemic action. Thus it proves possible to protect plants against fungal attack by supplying the active compound to the above-ground parts of the plant via the soil and the root.

As plant protection agents, the active compounds according to the invention can be used for the treatment of seed and of above-ground parts of plants. The active compounds have only low toxicity to warm-blooded animals and, because of their low odor and their good toleration by the human skin, are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules. etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylopolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides or insecticides, acaricides, nematocides, bactericides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–1.95% by weight, and preferably 0.5–90% by weight, of the mixture, whereas carrier composition mixtures suitable for direct application or field application generally contemplate those in which the active compound is present in an amount substantially between about 0.00001–10%, preferably 0.0001–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001–95%, and preferably 0.0001–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–1000 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially in the case of use as leaf fungicides, the active compound concentrations in the use forms can be varied within a substantial range. They are in general from 0.1 to 0.00001 percent by weight, and preferably from 0.05 to 0.0001 percent.

In the treatment of seed, amounts of active compound of 0.001 to 50 g per kilogram of seed, preferably 0.01 to 10 g, are in general required.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Erysiphe test (cucumbers)/protective

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus (*Erysiphe cichoriacearum*. The plants were subsequently placed in a greenhouse at 23°-24° C and at a relative atmospheric humidity of about 75%.

After 12 days, the infection of the cucumber plants was determined.

0% means no infection; 100% means that the plants were completely infected.

The active compounds, the concentrations of the active compounds and the results can be seen from the following table.

Table 1

Erysiphe test (cucumbers)/protective

| Active compound | Infection in % at an active compound concentration of 0.0025% |
|---|---|
| Ph-CH(Cl)-CH₂-N(imidazole) × HNO₃ (known) (A) | 31 |
| 2,4-Cl₂-C₆H₃-CH(Cl)-CH₂-N(imidazole) (2a) | 0 |
| 2,4-Cl₂-C₆H₃-CH(Cl)-CH₂-N(imidazole) × HNO₃ (2b) | 0 |
| 4-F-C₆H₄-CH(Cl)-CH₂-N(imidazole) (5) | 25 |
| 4-Cl-C₆H₄-C₆H₄-CH(Cl)-CH₂-N(imidazole) (1) | 0 |

EXAMPLE 2

Podosphaera test (powdery mildew of apples)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4-6 leaf stage were sprayed with the spray liquid until dripping wet. The plants remained in a greenhouse for 24 hours at 20° and at a relative atmospheric humidity of 70%. They were then inoculated by dusting with conidia of the apple powdery mildew causative organism (*Podosphaera leucotricha*) and placed in a greenhouse at a temperature of 21°-23° C and at a relative atmospheric humidity of about 70%.

10 days after the inoculation, the infection of the seedlings was determined.

0% means no infection; 100% means that the plants were completely infected.

The active compounds, the concentrations of the active compounds and the results can be seen from the following table:

Table 2

Podosphaera test/protective

| Active compound | Infection in % at an active compound concentration of 0.005% |
|---|---|
| Ph-CH(Cl)-CH₂-N(imidazole) × HNO₃ (known) (A) | 67 |
| 2,4-Cl₂-C₆H₃-CH(Cl)-CH₂-N(imidazole) (2a) | 25 |
| 2,4-Cl₂-C₆H₃-CH(Cl)-CH₂-N(imidazole) × HNO₃ (2b) | 30 |
| 4-F-C₆H₄-CH(Cl)-CH₂-N(imidazole) (5) | 27 |
| 4-Cl-C₆H₄-C₆H₄-CH(Cl)-CH₂-N(imidazole) (1) | 11 |

Table 2-continued

| Podosphaera test/protective | |
|---|---|
| Active compound | Infection in % at an active compound concentration of 0.005% |
| 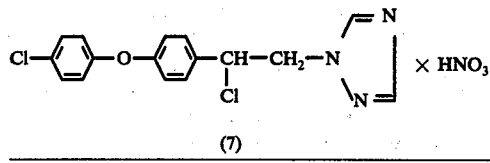 (7) | 7 |

EXAMPLE 3

Uromyces test (bean rust)/protective

Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated additives.

The young bean plants, which were in the 2-leaved stage, were sprayed with the spray liquor until dripping wet. The plants remained in a greenhouse for 24 hours at 20°–22° C and a relative atmospheric humidity of 70% in order to dry. They were then inoculated with an aqueous uredospore suspension of the causative organism of bean rust (*Uromyces phaseoli*) and incubated for 24 hours in a dark humidity chamber at 20°–22° C and 100% relative atmospheric humidity.

The plants were then set up in a greenhouse under intensive illumination for 9 days at 20°–22° C and a relative atmospheric humidity of 70–80%.

10 days after the inoculation, the infection of the plants was determined.

0% denotes no infection and 100% denotes that the plants were completely infected.

The active compounds, active compound concentrations and results can be seen from the following table:

Table 3

| Uromyces test/protective | |
|---|---|
| Active compound | Infection in % at an active compound concentration of 0.01% |
| 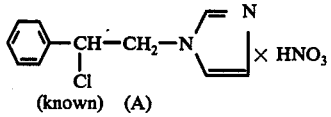 (known) (A) | 50 |
| 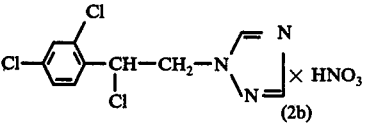 (2b) | 46 |
| 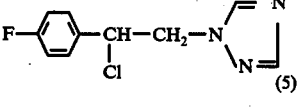 (5) | 46 |
| 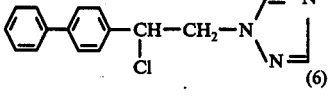 (6) | 46 |
| 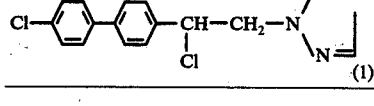 (1) | 0 |

EXAMPLE 4

Powdery mildew of barley (*Erysiphe graminis var. hordei*)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis var. hordei* and grown on at 21°–22° C and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denotes no infection and 100% denotes the same degree of infection as in the case of the untreated control. The active compound was the more active, the lower was the degree of mildew infection.

The active compounds and concentrations of active compound in the seed treatment agent, as well as the amount used of the latter, and the percentage infection with mildew can be seen from the table which follows:

added. The concentrate was diluted with water to the desired final concentration of the spray liquor.

To test for protective activity, single-leaved young barley plants of the Amsel variety were sprayed with the preparation of active compound until dew-moist. After drying, the young barley plants were dusted with spores of *Erysiphe graminis var. hordei*.

After 6 days' dwell time of the plants at a temperature

Table 4

Powdery mildew of barley test (*Erysiphe graminis var. hordei*)/systemic

| Active compounds | Active compound concentration in the dressing, in % by weight | Amount of dressing used in g/kg of seed | Infection in % of the untreated control |
|---|---|---|---|
| No dressing | — | — | 100.0 |
| CH₂—NHCS / CH₂—NHCS \ Zn (with C=S) (known) (B) | 30 | 10 | 100.0 |
| Cl-C₆H₃(Cl)-CH(Cl)-CH₂-N(imidazole) (2a) | 25 | 10 | 0.0 |
| Cl-C₆H₄-O-C₆H₄-CH(Cl)-CH₂-N(imidazole) × HNO₃ (7) | 25 | 10 | 25.0 |

EXAMPLE 5

Shoot treatment test/powdery mildew of cereals/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added.

of 21°–22° C and 80–90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The active compound was the more active, the lower was the degree of mildew infection.

The active compounds, active compound concentrations in the spray liquor and degrees of infection can be seen from the table which follows:

Table 5

Shoot treatment test/powdery mildew of cereals/protective

| Active compounds | Active compound concentration in the spray liquor in % by weight | Infection in % of the untreated control |
|---|---|---|
| Untreated | — | 100.0 |
| CH₂—NHCS / CH₂—NHCS \ Zn (with C=S) (known) (B) | 0.025 | 100.0 |
| Cl-C₆H₃(Cl)-CH(Cl)-CH₂-N(imidazole) × HNO₃ (2b) | 0.025 | 0.0 |

Table 5-continued

Shoot treatment test/powdery mildew of cereals/protective

| Active compounds | Active compound concentration in the spray liquor in % by weight | Infection in % of the untreated control |
|---|---|---|
| Cl—⟨⟩—O—⟨⟩—CH—CH$_2$—N⟨N=N⟩ (7)  × HNO$_3$ <br>               Cl | 0.025 | 0.0 |

EXAMPLE 6

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C and 100% relative atmospheric humidity.

After 10 days' dwell time of the plants at a temperature of 20° C and 80-90% atmospheric humidity, the occurrence of rust pustules on the plant was evaluated. The degree of infection was expressed as a percentage of the infection of the untreated control plants. 0% denotes no infection and 100% denotes the same degree of infection as in the case of the untreated control. The active compound was the more active, the lower was the degree of rust infection.

The active compounds, active compound concentrations in the spray liquor and degrees of infection can be seen from the table which follows:

Table 6

| Active compounds | Active compound concentration in the spray liquor in % by weight | Infection in % of the untreated control |
|---|---|---|
| Untreated | — | 100.0 |
| CH$_2$—NHCS$\diagdown$Zn <br> CH$_2$—NHCS$\diagup$ (known) (B) <br> (with S=C groups) | 0.025 | 93.8 |
| Cl—⟨Cl⟩—CH—CH$_2$—N⟨N=N⟩ (2a) <br>        Cl | 0.025 | 16.3 |
| Cl—⟨Cl⟩—CH—CH$_2$—N⟨N=N⟩ × HNO$_3$ (2b) <br>        Cl | 0.025 | 55.00 |
| ⟨⟩—⟨⟩—CH—CH$_2$—N⟨N=N⟩ (6) <br>        Cl | 0.025 | 0.0 |

EXAMPLE 7

Mycelium growth test
Nutrient medium used:
   20 parts by weight of agar-agar
   200 parts by weight of potato decoction
   5 parts by weight of malt
   15 parts by weight of dextrose
   5 parts by weight of peptone
   2 parts by weight of disodium hydrogen phosphate
   0.3 part by weight of calcium nitrate
Composition of the solvent mixture:
   0.19 part by weight of acetone
   0.01 part by weight of emulsifier (Emulvin W)
   1.80 parts by weight of water
Ratio of solvent mixture to nutrient medium:
   2 parts by weight of solvent mixture
   100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

cined potassium carbonate and 13 g (0.2 mole) of 1,2,4-triazole in 200 ml of acetone were heated to the boil for 12 hours, while stirring. 800 ml of water were added to the suspension when it had cooled, and the mixture was filtered. The solid reaction product was recrystallized from isopropanol/dimethylformamide. 17.1 g (57% of theory) of ω-[1,2,4-triazolyl-(1)]-4-(4'-chlorophenyl)-acetophenone of meltingpoint 213° C were obtained.

b) 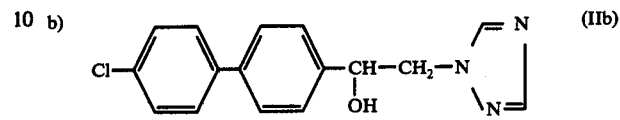 (IIb)

150 g (0.5 mole) of ω-[1,2,4-triazolyl-(1)]-4-(4'-chlorophenyl)-acetophenone were dissolved in 1 liter of methanol and 23 g (0.55 mole) of sodium borohydride were added in portions at 0° to 10° C, while stirring. The Table 7

| | Mycelium growth test | | | | | | | | | | |
|---|---|---|---|---|---|---|---|---|---|---|---|
| | Fungi | | | | | | | | | | |
| Active compound concentration =10 ppm<br>Active compounds | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Pellicularia sasakii |
| (known) (A) | 9 | 9 | 9 | 9 | 9 | 9 | 9 | 9 | 9 | 9 | 9 |
| (2a) | 2 | 2 | 5 | 3 | 1 | 5 | 2 | 1 | 3 | 5 | |
| (2b) | 2 | 5 | 5 | | | 5 | 3 | 1 | | 5 | |
| (2) | 5 | 2 | 3 | 3 | 1 | 3 | 3 | 1 | | 5 | |
| (7) | 5 | 1 | 1 | | 5 | 5 | 3 | 3 | 1 | | 2 |

The process according to the present invention is illustrated by the following preparative examples:

EXAMPLE 8 a) 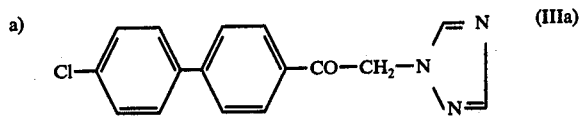 (IIIa)

31 g (0.1 mole) of ω-bromo-4-(4'-chlorophenyl)acetophenone together with 13.8 g (0.1 mole) of calmixture was then stirred for one hour at room temperature and heated to the boil for one hour. After distilling off the solvent, the residue was briefly heated with 1 liter of water and 300 ml of concentrated hydrochloric acid. After the reaction mixture had been rendered alkaline with sodium hydroxide solution, the solid reaction product could be filtered off. 140 g (97% of theory) of 1-(2-[4''-chloro-4'-biphenylyl]-2-hydroxyethyl)-1,2,4-triazole of melting point 199° C were obtained.

a) 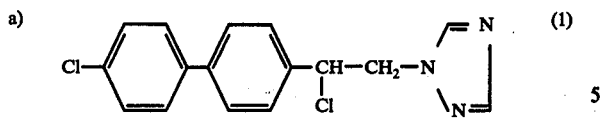

150 g (0.5 mole) of 1-(2-[4''-chloro-4'-biphenylyl]-2-hydroxy-ethyl)-1,2,4-triazole were dissolved in 2 liters of chloroform and heated to the boil, while stirring. 90g (0.75 mole) of thionyl chloride were slowly added dropwise thereto. The reaction mixture was heated for 12 hours under reflux and after cooling, 1.5 liters of toluene were added. The hydrochloride of 1-(2-chloro-2-[4'(4''-chlorophenyl)-phenyl]-ethyl)-1,2,4-triazole, which thereupon precipitated, was filtered off and taken up in 2 liters of water. The free base was obtained by adding sodium bicarbonate, and was taken up in chloroform. After drying over sodium sulfate, the solvent was distilled off and the residue soldified to crystals. 148 g (92% of theory) of 1-(2-chloro-2-[4''-chloro-4'-biphenylyl]ethyl)-1,2,4-triazole of melting point 118° C were obtained.

EXAMPLE 9

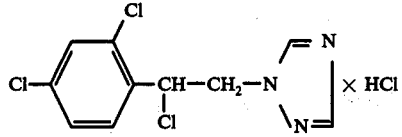

129 g (0.5 mole) of 1-(2-[2',4'-dichlorophenyl]-2-hydroxy-ethyl)-1,2,4-triazole were dissolved in 1 liter of chloroform and the solution was heated to the boil while stirring. 90 g (0.75 mole) of thionyl chloride were slowly added dropwise. After heating for several hours under reflux, the mixture was allowed to cool, and 1 liter of toluene was added. The hydrochloride which had precipitated was filtered off and washed with petroleum ether. 150 g (96% of theory) of 1-(2-chloro-2-[2',4'-dichlorophenyl]-ethyl)-1,2,4-triazole hydrochloride of melting point 160° C were obtained.

EXAMPLE 10

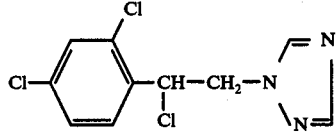

25.8 g (0.1 mole) of 1-(2-[2',4'-dichlorophenyl]-2-hydroxy-ethyl)-1,2,4-triazole were dissolved in 150 ml of chloroform and the solution was heated to the boil while stirring. 14.5 g (0.12 mole) of thionyl chloride were slowly added dropwise. The mixture was stirred for several more hours while boiling under reflux. After it had cooled, 250 ml of toluene were added to the reaction mixture. The hydrochloride of 1-(2-chloro-2-[2',4'-dichlorophenyl]-ethyl)-1,2,4-triazole, which thereupon precipitated, was filtered off and treated with water/sodium bicarbonate. The free base thereby produced was taken up in ethyl acetate. After drying over sodium sulfate, the solvent was distilled off and the residue was caused to crystallize by digesting with petroleum ether. 16.8 g (70% of theory) of 1-(2-chloro-2-[2',4'-dichlorophenyl]-ethyl)-1,2,4-triazole of melting point 67° C were obtained.

EXAMPLE 11

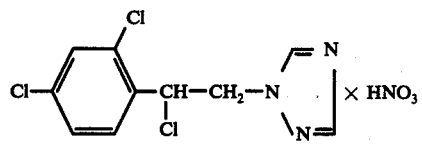

27.7 g (0.1 mole) of 1-(2-chloro-2-[2',4'-dichlorophenyl]-ethyl)-1,2,4-triazole (see Example 10) were dissolved in 200 ml of chloroform and 7 g of 95% strength nitric acid (d-1.50) were added while cooling with ice. Crystallization was completed by adding 600 ml of ether. The crystalline product was filtered off and dried. 27 g (92% of theory) of 1-(2-chloro-2-[2',4'-dichlorophenyl]-ethyl)-1,2,4-triazole nitrate of melting point 162° C were obtained.

EXAMPLE 12

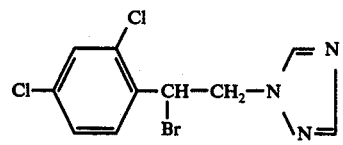

25.8 g (0.1 mole) of 1-(2-[2',4'-dichlorophenyl]-2-hydroxy-ethyl)-1,2,4-triazole were dissolved in 200 ml of chloroform and 27 g (0.1 mole) of phosphorus tribromide were added, whereupon the temperature rose to 45° C. The mixture was heated for 3 hours under reflux. After it had cooled, a solution of 25.5 g (0.3 mole) of sodium bicarbonate in 150 ml of water was added to the reaction mixture. The organic phase was separated off and dried over sodium sulfate, and the solvent was distilled off. The oily residue crystallized on trituration with petroleum ether. 17.2 g (54% of theory) of 1-(2-bromo-2-[2',4'-dichlorophenyl]-ethyl)-1,2,4-triazole of melting point 97° C were obtained.

The following compounds of the general formula

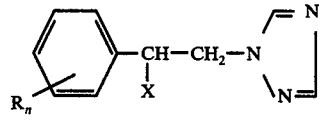

were obtained by analogous procedures:

Table 8

| Compound No. | $R_n$ | X | Melting point |
| --- | --- | --- | --- |
| 4 | 4-Cl | Cl | viscous oil |
| 5 | 4-F | Cl | viscous oil |
| 6 | 4-C$_6$H$_5$ | Cl | 105 |
| 7 | 4-O—⟨phenyl⟩—Cl | Cl | 155 (nitrate) |

Other compounds which can be similarly prepared include:

Table 9

| $R_n$ | X |
| --- | --- |
| 4-CF$_3$ | F |
| 3-CN | Cl |
| 2-Br-4-C$_3$H$_7$-iso | Cl |

Table 9-continued

| $R_n$ | X |
| --- | --- |
| 4-NO$_2$ | Cl |
| 4-CH$_3$SO$_2$— | Cl |
| 4-n-C$_4$H$_9$O— | Cl |
| 4-C$_2$H$_5$S— | Cl |
| 4-C$_6$H$_5$O— | Cl |
| 2-(4'-CN—C$_6$H$_5$)— | Cl |
| 3-(3'-CF$_3$—C$_6$H$_5$O)— | Cl |
| 4-(4'-NO$_2$—C$_6$H$_5$)— | Cl | and the like.

It will be appreciated that the instant specification and examples are set forth by way of illustration and not limitation, and that various modifications and changes may be made without departing from the spirit and scope of the present invention.

What is claimed is:

1. A compound of the formula

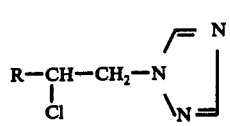

in which R is

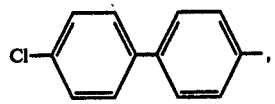

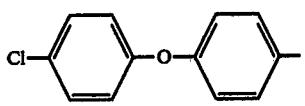

or 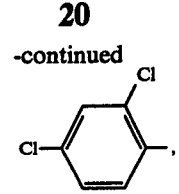

or a salt thereof with a physiologically tolerated acid.

2. A compound according to claim 1 wherein such compound is 1-(2-chloro-2-[4''-chloro-4'-biphenylyl]-ethyl)-1,2,4-triazole of the formula

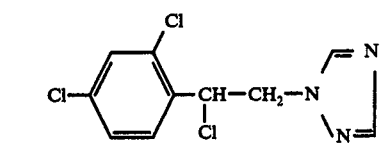

or a salt thereof with a physiologically tolerated acid.

3. A compound according to claim 1 wherein such compound is 1-(2-chloro-2-[2',4'-dichlorophenyl]-ethyl)-1,2,4-triazole of the formula

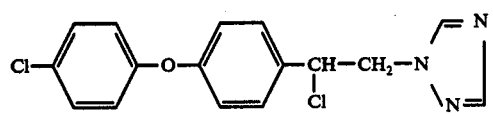

or a salt thereof with a physiologically tolerated acid.

4. A compound according to claim 1 wherein such compound is 1-(2-chloro-2-[4''-chlorophenoxyphenyl]-ethyl)-1,2,4-triazole of the formula or a salt thereof with a physiologically tolerated acid.

* * * * *